US00PP15387P2

(12) United States Plant Patent
Gass

(10) Patent No.: US PP15,387 P2
(45) Date of Patent: Nov. 30, 2004

(54) ***CALLIANDRA* PLANT NAMED 'LIANCA'**

(50) Latin Name: *Calliandra eriophylla×californica*
Varietal Denomination: Lianca

(76) Inventor: Ronald E. Gass, 10020 W. Glendale Ave., Glendale, AZ (US) 85307

( * ) Notice: Subject to any disclaimer, the term of this patent is extended or adjusted under 35 U.S.C. 154(b) by 0 days.

(21) Appl. No.: 10/703,001

(22) Filed: Nov. 5, 2003

(51) Int. Cl.[7] ..... A01H 5/00
(52) U.S. Cl. ..... Plt./226
(58) Field of Search ..... Plt./226

*Primary Examiner*—Kent Bell
(74) *Attorney, Agent, or Firm*—Joseph H. Roedlger; Gregory J. Nelson

(57) ABSTRACT

A new and distinct hybrid of the genus *Calliandra* is provided. This hybrid has been name 'Lianca' for a cultivar name and is trademarked as Sierra Starr™. The new variety is a product of a deliberate cross of *Calliandra eriophylla* and *Calliandra californica* made in 1982.

Seeds from this cross were saved and planted. The new variety was selected from a block of these hybrid seedlings. The new variety displays a distinctly different flower color previously unavailable in the genus.

3 Drawing Sheets

Genus and species of the plant:

The subject plant is a new and distinct hybrid of the genus *Calliandra*. The new variety is a product of a deliberate cross of *Calliandra eriphylla* and *Calliandra california*. The Genus/species designation for the plant is *Calliandra eriophylla×california*.

The present invention comprises a new and distinct variety of the *Calliandra* plant and hereinafter is referred to by the variety name 'Lianca'. Sierra Starr is a trade mark applied to the variety to indicate the source of origin thereof.

BACKGROUND OF THE INVENTION

The new 'Lianca' variety was selected by me as a single plant from a block of hybrid seedlings during the course of plant breeding work in the year 1982. The hybrid seedlings were a result of a cross between an unnamed plant of *Calliandra eriophylla* and an unnamed plant of *Calliandra californica*. The *Calliandra eriophylla* plant and the *Calliandra californica* plant are unpatented selections from native populations. The *Calliandra eriophylla* is the female parent in the cross that yielded the seedling which is the *Calliandra* plant 'Lianca', the subject of this plant patent application. Seeds from this cross were saved and planted. The new variety was selected from a block of these hybrid seedlings.

SUMMARY OF THE INVENTION

The new variety *Calliandra* 'Lianca' is distinguishable from its parents by displaying a distinctly different flower color previously unavailable in the genus *Calliandra*. This color is displayed in filament and style of this plant and is a primary distinguishing characteristic of the new variety. The distinctive red color is identified as R.H.S. Red Group 53C.

The seedlings were grown for about 5 years and a selection was made based on the color of the filament and style. The selected seedling was grown for 3 additional years and the distinctive color distinguished this seedling from other seedlings. Thereafter, asexual propagation of this new variety was carried out in Glendale, Ariz. by cuttings through several generations. The new variety reproduces true to type in successive generations of asexual reproduction. The distinctive red color of filament and style remain constant in each successive crop of cutting-grown plants. The following detailed description is taken from plants that have been growing in a ground bed for four years.

The *Calliandra* 'Lianca' is a bush with an upright growth habit to 1.5 meters. The new 'Lianca' variety exhibits heavy side branching similar to the *Calliandra eriophylla* branching habit to achieve a plant width to 1.5 meters. The 'Lianca' plant is deciduous and at temperature exposures about 30° F. is characterized as reluctantly deciduous. The maximum winter hardiness is USDA Zone 8.

This hybrid plant is not known to be susceptable to any soil borne pathogens or to any foliar disease. The plant has not been observed to suffer from any insect infestations.

BRIEF DESCRIPTION OF THE DRAWINGS

The accompanying photographic drawings show typical specimens of plant parts of the new variety in color illustrations as nearly true as is reasonably possible to accomplish from conventional photographic procedures.

Figure 1:
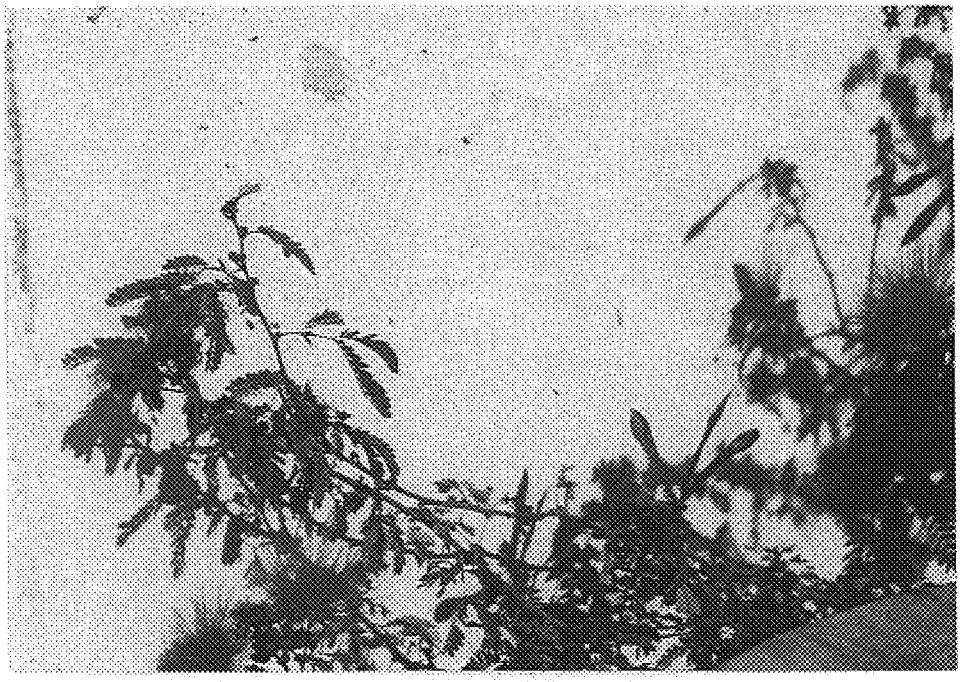
FIG. 1 shows side branching of the 'Lianca' plant as appearing during the autumn season.
Figure 2:
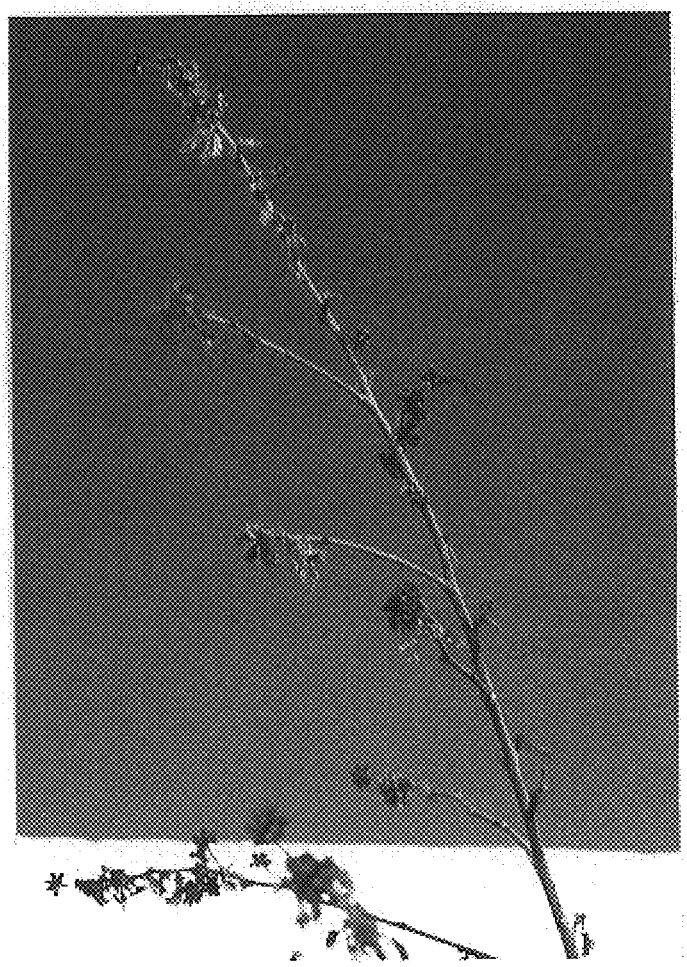
FIG. 2 shows branching of the 'Lianca' plant as appearing during the winter season.
Figure 3:
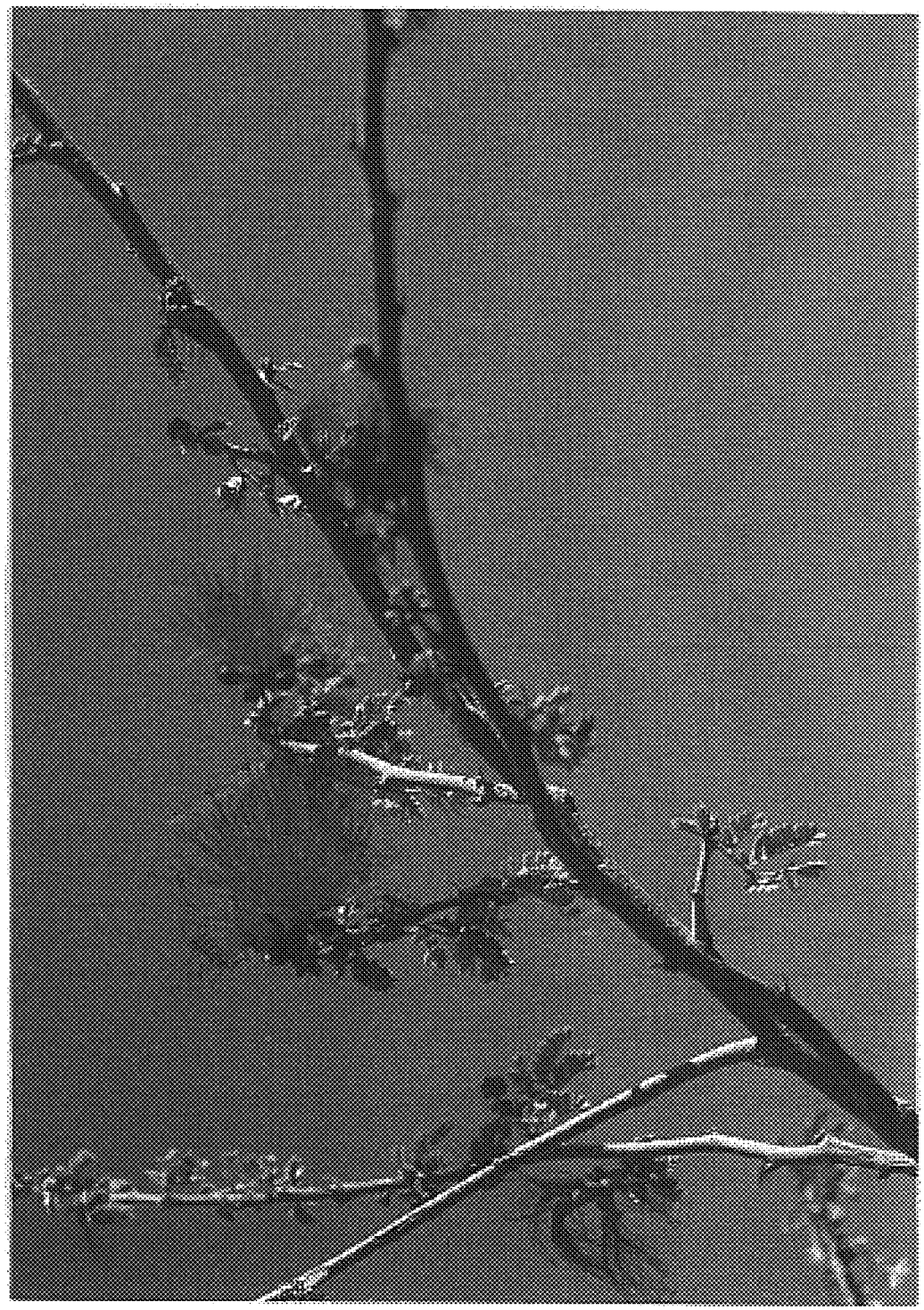
FIG. 3 shows a close up of the flower and leaves during the winter season.
Figure 4:
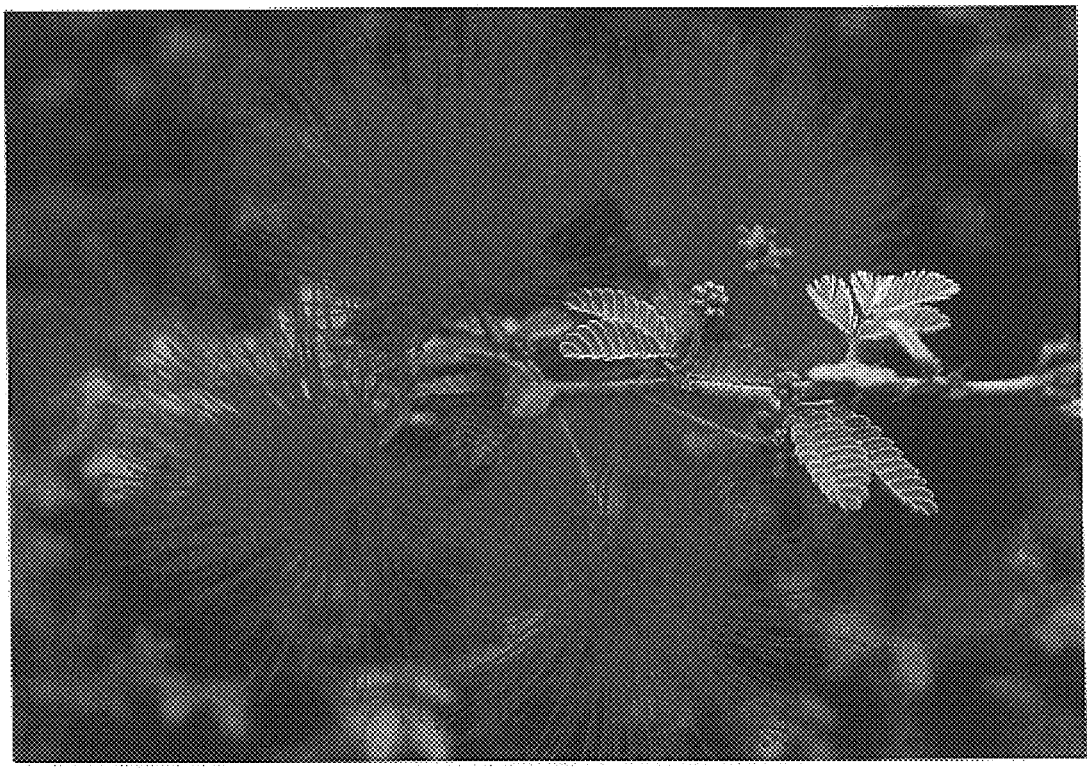
FIG. 4 shows the leaves, branches and flowers during the spring season.
Figure 5:
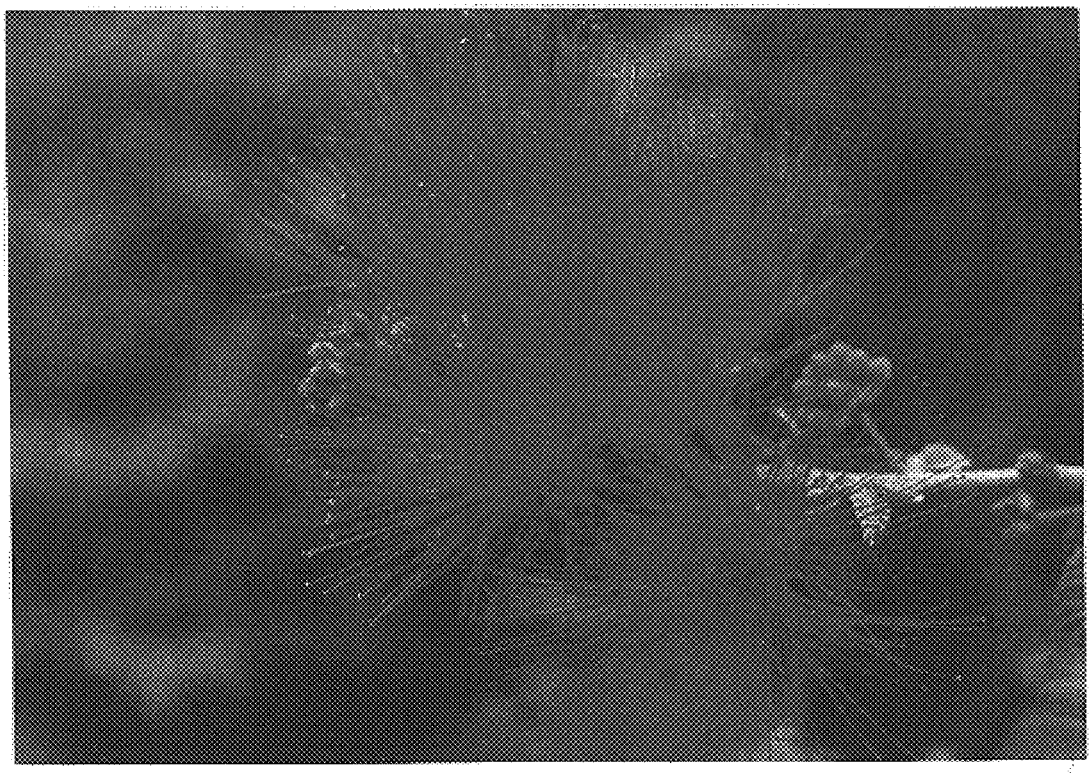
FIG. 5 shows a close up of the flower during the spring season.

The color chart used in the identification of colors described herein is The R.H.S. Colour Chart of The Royal Horticultural Society, London, England. The plants described were grown during 2001–2002 at Glendale, Ariz.

DETAILED BOTANICAL DESCRIPTION

Description of the plant:

*Classification.*—*Calliandra* Hybrid.

*Plant form.*—Bush.
*Plant height.*—To 1½ meters.
*Plant width.*—To 1½ meters.
*Plant growth habit.*—Perennial, upright shrub with heavy side branching similar to the *Calliandra eriophylla* branching habit.
*Stem/lateral branch diameter.*—2–5 millimeters.
*Stem/lateral branch internode.*—2–3 centimeters.

Foilage description:
*Leaf arrangement.*—Alternate.
*Stipules.*—Linear, 2–5 mm in length.
*Petiole length.*—4–14 millimeters.
*Petiole diameter.*—0.5–1 millimeter.
*Petiole color.*—RHS Yellow Green Group 135A.
*Leaf shape.*—Bipinnately compound.
*Leaf length.*—Pinnae — 2 pairs 9–40 mm long.
*Leaf width.*—40–90 millimeters.
*Leaflets.*—5–12 pairs 3–8 mm long, 2–3 mm wide, oblong-elliptic.
*Leaflet base.*—Asymmetrical cordate.
*Leaflet apex.*—Mucronate.
*Leaflet pubescence.*—Finely appressed puberulent on both surfaces.
*Leaflet margin.*—Entire.
*Leaflet color.*—Upper surface RHS Yellow Green Group 135 A—uniform over surface; underside RHS Yellow Green Group 137 B—uniform over surface.
*Rachis.*—RHS Yellow Green Group 152 C, underside transitioning to RHS Greyed Purple Group 187 B on upper side in early winter.

Leaves are seasonally uniform to these measurements and colors except in winter when deciduous. Reluctantly deciduous at temperature exposures above 30° F.

Description of the flower:
*Inflorescence type.*—Capitate heads.
*Peduncle length.*—16–22 mm.
*Peduncle diameter.*—0.9–1.0 millimeter.
*Peduncle color.*—RHS Yellow Green Group 144A.
*Flower number.*—8–13.
*Calyx.*—5 toothed.
*Calyx shape.*—Tubular-funnelform.
*Calyx length.*—1.8–2.2 mm.
*Calyx width.*—1.5–2 mm.
*Calyx pubescence.*—Minutely pubescent with closely appressed fine hairs on outer surface.
*Calyx color.*—RHS Yellow Green Group 145 C overall.
*Corolla shape.*—Funnelform with 3–5 lobes.
*Corolla height.*—7–9 mm including lobes.
*Corolla lobe length.*—3–4 mm recurving to as much as 1½ revolutions with age.
*Corolla diameter.*—3–4 mm before lobes recurve with age, 4–4.5 mm after lobes recurve.
*Corolla lobes.*—Elliptic lanceolate, 2–3 mm wide, 5 mm long, apex obtuse to acute, fused based, entire margins.
*Corolla color.*—At base RHS Yellow Green Group 145 C; at midpoint of the length of the corolla color grades to RHS 46B.
*Corolla pubescence.*—Minutely pubescent with closely appressed fine hairs on outer surface.
*Pistil.*—1 pistil per flower.
*Style length.*—25–29 mm.
*Style color.*—RHS Red Group 53 C.
*Stigma.*—Capitate, glabrous.
*Stigma width.*—0.2–0.3 mm.
*Filament number.*—29–35.
*Filament length.*—22–29 mm.
*Filament color.*—RHS Red Group 53 C, the color of the filaments and style are unique to this hybrid. This color is its main distinguishing characteristic.
*Pollen.*—Scarce.
*Pollen color.*—Cream (too small and scarce to use color chart).
*Fruit.*—Indistinguishable from either parent.
*Seeds.*—Indistinguishable from either parent.

What is claimed is:

1. A new and distinct variety of *Calliandra* plant as herein illustrated and described.

* * * * *